United States Patent [19]

Holton

[11] Patent Number: 5,574,156
[45] Date of Patent: *Nov. 12, 1996

[54] β-LACTAMS USED IN PREPARING TAXOL

[75] Inventor: Robert A. Holton, Tallahassee, Fla.

[73] Assignee: Florida State University, Tallahassee, Fla.

[*] Notice: The term of this patent shall not extend beyond the expiration date of Pat. No. 5,539,103.

[21] Appl. No.: 254,561

[22] Filed: Jun. 6, 1994

Related U.S. Application Data

[62] Division of Ser. No. 968,003, Oct. 26, 1992, Pat. No. 5,336,785, which is a continuation of Ser. No. 415,028, Sep. 29, 1989, Pat. No. 5,175,315, which is a continuation-in-part of Ser. No. 359,634, May 31, 1989, abandoned, which is a continuation of Ser. No. 967,998, Oct. 26, 1992, abandoned, which is a division of Ser. No. 415,028, Sep. 29, 1989, Pat. No. 5,175,315, which is a continuation-in-part of Ser. No. 359,634, May 31, 1989, abandoned, said Ser. No. 967,998, is a division of Ser. No. 949,107, Sep. 22, 1992, abandoned.

[51] Int. Cl.[6] ..................... C07D 205/08; C07D 305/14; C07C 233/87
[52] U.S. Cl. ........................ 540/357; 540/354; 540/360
[58] Field of Search ..................................... 540/354, 357, 540/360

[56] References Cited

U.S. PATENT DOCUMENTS

| | | | |
|---|---|---|---|
| 4,680,391 | 7/1987 | Firestone et al. | 540/355 |
| 4,814,470 | 3/1989 | Colin et al. | 514/449 |
| 4,857,653 | 8/1989 | Colin et al. | 549/511 |
| 4,924,011 | 5/1990 | Denis et al. | 849/510 |
| 4,924,012 | 5/1990 | Colin et al. | 849/510 |
| 5,105,744 | 5/1991 | Holton | 549/510 |
| 5,136,060 | 8/1992 | Holton | 549/510 |
| 5,175,315 | 12/1992 | Holton | 549/510 |
| 5,254,580 | 10/1993 | Chen et al. | 514/449 |
| 5,272,171 | 12/1993 | Ueda et al. | 514/449 |
| 5,284,864 | 2/1994 | Holton et al. | 514/449 |

FOREIGN PATENT DOCUMENTS

| | | |
|---|---|---|
| 023097 | 1/1981 | European Pat. Off. . |
| 146900 | 7/1985 | European Pat. Off. . |
| 247378 | 9/1990 | European Pat. Off. . |
| 582469 | 2/1994 | European Pat. Off. . |
| 200155 | 8/1985 | New Zealand . |
| 1349357 | 4/1974 | United Kingdom . |

OTHER PUBLICATIONS

A. K. Mukerjee et al. "Synthesis of B–Lactams" Synthesis, No. 6, pp. 327–346 (1973).
A. K. Bose et al. "Studies on the Mechanism of B–lactam Formation" Tetrahedron Letters, No. 40, pp. 4091–4094 (1972).
A. K. Bose et al. "Studies on Lactams. Part XVI. Stereochemistry of B–lactam Formation" Tetrahedron Letters, No. 34, pp. 3167–3170 (1971).
T. W. Doyle et al. "Nuclear Analogs of B–lactam Antibiotics. I. Synthesis of O–2–isocephams" Canadian Jour. of Chemistry, vol. 55, pp. 468–483 (1977).

A. K. Bose et al. "Studies on B–lactams. XXXVI. Monocyclic Cis B–lactams via Penams and Cephams" Journal of Organic Chemistry, vol. 39, No. 19, pp. 2877–2884 (1974).
J. N. Wells et al. "The Synthesis of 2–Azetidinones" Journal of Organic Chemistry, vol. 34, No. 5, pp. 1477–1479 (1969).
A. K. Bose et al. "Studies on Lactams–V 3–Azido–2–Azetidinones" Tetrahedron Letters, vol. 23, pp. 4769–4776 (1967).
Hawley's Condensed Chemical Dictionary, 12th Ed., Van Nostrand Reinhold Co., pp. 21–22 (1993).
Zakhs et al. "Oxo Derivatives of 1,3–Oxazines" Chemistry of Heterocyclic Compounds, vol. 11 (1987) pp. 1147–1166.
Denis and Greene "A Highly Efficient, Practical Approach to Natural Taxol" Journal of American Chemical Society, vol. 110 (1988) pp. 5917–5919.
Holton et al. "A Synthesis of Taxusin" Journal of American Chemical Society, vol. 110 (1988) pp. 6558–6560.
Holton "Synthesis of the Taxane Ring System" Journal of American Chemical Society, vol. 106 (1984) pp. 5731–5732.
Ojima et al. "New and Efficient Approaches to the Semisynthesis of Taxol and its C–13 Side Chain Analogs by Means of B–Lactam Synthon Method" Tetrahedron Letters vol. 48, No. 34 (1992) pp. 6985–7012.
Bose et al. "Studies on Lactams–Vl 3j–Azido–2–Azetidinones" Tetrahedron Letters vol. 23 (1967) pp. 4769–4776.
Hart et al. "The Ester Enolate–Imine Condensation Route to β–Lactams" Chemical Review, vol 38 (1989) pp. 1447–1465.
Mukerjee et al. "β–Lactams: Retrospect and Prospect" Tetrahedron Letters vol. 34, No. 52 (1978) pp. 1731–1767.
Bartholomew et al. "A Novel Rearrangement Reaction Conversion of 3–(chloromethyl)azetidin–2–ones to Azetidine–3–carboxylic Acid Esters" Tetrahedron Letters, vol. 32, No. 36 (1991) pp. 4795–4798.
Schultz et al. "Synthesis of New N–radicals of Tetrazan–1–yl" Chemical Abstract, vol. 108, No. 37298C (1988) P. 581.

(List continued on next page.)

Primary Examiner—Mark L. Berch
Attorney, Agent, or Firm—Senniger, Powers, Leavitt & Roedel

[57] ABSTRACT

A β-lactam of the formula:

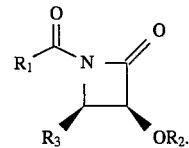

wherein $R_1$ is aryl, substituted aryl, alkyl, alkenyl, or alkynyl; $R_2$ is hydrogen, alkyl, acyl, acetal, ethoxyethyl, or other hydroxyl protecting group; and $R_3$ is aryl, substituted aryl, alkyl, alkenyl, or alkynyl; and the enantiomers and diastereomers thereof.

19 Claims, No Drawings

OTHER PUBLICATIONS

Steglich et al. "1,3-oxazin-6-ones: Versatile Intermediates In Heterocyclic Synthesis" Research Report, Gazzetta Chemica Italiana, 116 (1986) pp. 361–372.

Murkerjee "Reactions of Natural and Synthetic β-Lactams" Synthesis (1975) pp. 547–590.

Kingston et al. "Progress in the Chemistry of Organic Natural Products" Springer Verlag, Wien New York (1993) pp. 145–150.

Evans et al. "The Asymmetric Synthesis of β-lactam Antibotics-I. Application of Chiral Oxazolidones in the Staudinger Reaction" Tetrahedron Letters, vol. 26, No. 32 (1985) pp. 3783–3786.

Hart et al. "Asymmetric Synthesis of β-lactams and the Carbapenem Antibiotic (+)-PS-5" Journal of American Chemical Society, vol. 108 (1986) pp. 6054–6056.

Burnett et al. "Synthesis of 3-(1-Hydroxyethyl)-2-azetidin-ones via Ester-Imine Condensations" Journal of Organic Chemistry, vol 50 (1989) pp. 5120–5123.

Cossia et al. "Triphenylphosphine Dibromide and Dimethyl-Sulfide Dibromide As Versatile Reagents For β-Lactam Synthesis" Tetrahedron Letters, vol. 26, No. 25 (1985) pp. 3041–3044.

Georg et al. "Stereocontrolled Ketene-Imine Cycloaddition Reactions" The Organic Chemistry of β-lactams, Chapter 6, pp. 295–368. (1982).

Cluchowski et al. "Preparation of β-lactams by the Condensation of Lithium Ester Enolates With Aryl Aldimines", Journal of Organic Chemistry, vol. 45 (1980) pp. 3413–3416.

C. Palomo et al. "Highly Stereoselective Synthesis of α-Hydroxy β-Amino Acids Through β-Lactams: Application to the Synthesis of the Taxol and Bestatin Side Chains and Related Systems" Tetrahedron Letters, 31:44 (1990) pp. 6429–6432.

β-LACTAMS USED IN PREPARING TAXOL

This invention was made with Government support under NIH Grant #CA 42031 awarded by the National Institute of Health. The Government has certain rights in the Invention.

CROSS-REFERENCE TO RELATED APPLICATION

This application is a divisional of U.S. Ser. No. 07/968,003, filed Oct. 26, 1992, now U.S. Pat No. 5,336,785, which is a continuation of U.S. Ser. No. 07/415,028, filed Sep. 29, 1989, now U.S. Pat. No. 5,175,315, which is a continuation-in-part of U.S. Ser. No. 07/359,634, filed May 31, 1989, now abandoned which is a continuation of U.S. Ser. No. 07/967,998, filed Oct. 26, 1992, now abandoned which is a divisional application of U.S. Ser. No. 07/415,028, filed Sep. 29, 1989, now U.S. Pat. 5,175,315, which is a continuation-in-part of application Ser. No. 07/359,634, filed May 31, 1989, now abandoned. U.S. Ser. No. 967,998, filed Oct. 26, 1992 is also a divisional application of U.S. Ser. No. 07/949,107, filed Sep. 22, 1992, now abandoned.

BACKGROUND OF THE INVENTION

The present invention is directed to novel β-lactams, a process for their preparation, and a process for the preparation of taxol involving the use of such β-lactams.

The taxane family of terpenes, of which taxol is a member, has attracted considerable interest in both the biological and chemical arts. Taxol is a promising cancer chemotherapeutic agent with a broad spectrum of antileukemic and tumor-inhibiting activity, having the following structure:

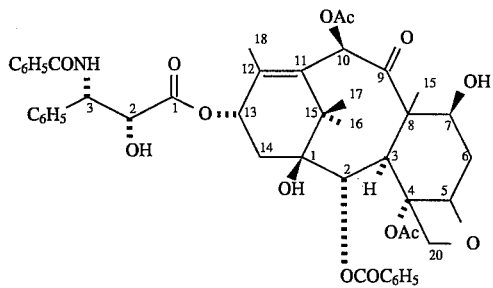

Because of this promising activity, taxol is currently undergoing clinical trials in both France and the United States.

The supply of taxol for these clinical trials is presently being provided by the bark from several species of yew. However, taxol is found only in minute quantities in the bark of these slow growing evergreens, causing considerable concern that the limited supply of taxol will not meet the demand. Consequently, chemists in recent years have expended their energies in trying to find a viable synthetic route for the preparation of taxols. So far, the results have not been entirely satisfactory.

One synthetic route that has been proposed is directed to the synthesis of the tetracyclic taxane nucleus from commodity chemicals. A synthesis of the taxol congener taxusin has been reported by Holton, et al. in JACS 110, 6558 (1988). Despite the progress made in this approach, the final total synthesis of taxol is, nevertheless, likely to be a multi-step, tedious, and costly process.

An alternate approach to the preparation of taxol has been described by Greene, et al. in JACS 110, 5917 (1988), and involves the use of a congener of taxol, 10-deacetyl baccatin III which has the structure shown below:

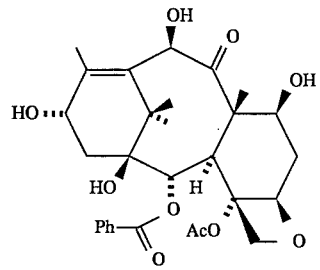

10-deacetyl baccatin III is more readily available than taxol since it can be obtained from the leaves of *Taxus baccata*. According to the method of Greene et al., 10-deacetyl baccatin III is converted to taxol by attachment of the C10 acetyl group and by attachment of the C13 β-amido ester side chain through the esterification of the C-13 alcohol with a β-amido carboxylic acid unit. Although this approach requires relatively few steps, the synthesis of the β-amido carboxylic acid unit is a multi-step process which proceeds in low yield, and the coupling reaction is tedious and also proceeds in low yield. However, this coupling reaction is a key step which is required in every contemplated synthesis of taxol or biologically active derivative of taxol, since it has been shown by Wani, et al. in JACS 93, 2325 (1971) that the presence of the β-amido ester side chain at C13 is required for anti-tumor activity.

A major difficulty remaining in the synthesis of taxol and other potential anti-tumor agents is the lack of a readily available unit which could be easily attached to the C13 oxygen to provide the β-amido ester side chain. Development of such a unit and a process for its attachment in high yield would facilitate the synthesis of taxol as well as related anti-tumor agents having a modified set of nuclear substituents or a modified C13 side chain. This need has been fulfilled by the discovery of a new, readily available, side chain precursor chemical unit and an efficient process for its attachment at the C13 oxygen.

SUMMARY OF THE INVENTION

Among the objects of the present invention, therefore, is the provision of a side chain precursor for the synthesis of taxols, and the provision of a process for the attachment of the side chain precursor in relatively high yield to provide a taxol intermediate.

Briefly, therefore, the present invention is directed to a side chain precursor, a β-lactam 1 of the

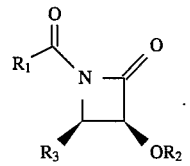

wherein $R_1$ is aryl, substituted aryl, alkyl, alkenyl, or alkynyl; $R_2$ is hydrogen, ethoxyethyl, acetal, or other hydroxyl protecting group; and $R_3$ is aryl, substituted aryl, alkyl, alkenyl, or alkynyl.

The present invention is also directed to a process for the preparation of a taxol intermediate comprising contacting an alcohol with β-lactam 1 in the presence of a sufficient amount of an activating agent under effective conditions to cause the β-lactam to react with the alcohol to form a

3

β-amido ester which may be used as an intermediate in the synthesis of taxol.

The present invention is also directed to a process for the preparation of taxol which comprises contacting an alcohol with β-lactam 1 in the presence of a sufficient amount of an activating agent under effective conditions to cause the β-lactam to react with the alcohol to form a β-amido ester taxol intermediate. The intermediate is then used in the synthesis of taxol.

Other objects and features of this invention will be in part apparent and in part pointed out hereinafter.

DETAILED DESCRIPTION

The present invention is directed to a β-lactam 1 and its derivatives, the structure of which is depicted hereinbelow.

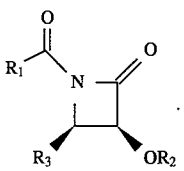

As noted above, $R_1$ is aryl, substituted aryl, alkyl, alkenyl, or alkynyl; $R_2$ is hydrogen, ethoxyethyl, acetal or other hydroxyl protecting group; and $R_3$ is aryl, substituted aryl, alkyl, alkenyl, or alkynyl. Preferably, $R_1$ is phenyl, substituted phenyl, or aryl; $R_2$ is ethoxyethyl, 2,2,2-trichloroethoxymethoxy, or other acetal hydroxyl protecting group; and $R_3$ is phenyl, substituted phenyl, or aryl. Structures of two of the preferred β-lactams in which $R_1$ and $R_3$ are phenyl, are shown below:

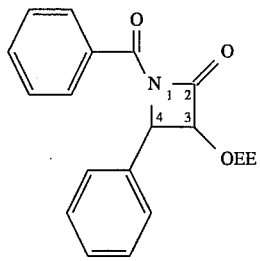

2

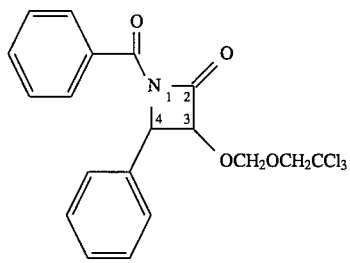

3

According to IUPAC rules, the names of β-lactams 2 and 3 are 1-Benzoyl-4-phenyl-3-(1-ethoxyethoxy)azetidin-2-one 2, and 1-Benzoyl-4-phenyl-3-(2,2,2-trichloroethoxymethoxy) azetidin-2-one 3. The most preferred β-lactam is β-lactam 2.

In accordance with the present invention, a process is provided for preparing taxol intermediates, natural taxol and non-naturally occurring taxols having the following structural formula:

4

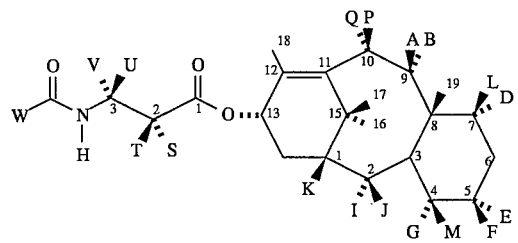

wherein

A and B are independently hydrogen or lower alkanoyloxy, alkenoyloxy, alkynoyloxy, or aryloyloxy or A and B together form an oxo;

L and D are independently hydrogen or hydroxy or lower alkanoyloxy, alkenoyloxy, alkynoyloxy, or aryloyloxy;

E and F are independently hydrogen or lower alkanoyloxy, alkenoyloxy, alkynoyloxy, or aryloyloxy or;

E and F together form an oxo;

G is hydrogen or hydroxy or lower alkanoyloxy, alkenoyloxy, alkynoyloxy, or aryloyloxy or G and M together form an oxo or methylene or G and M together form an oxirane ring or M and F together form an oxetane ring;

J is hydrogen, hydroxy, or lower alkanoyloxy, alkenoyloxy, alkynoyloxy, or aryloyloxy or I is hydrogen, hydroxy, or lower alkanoyloxy, alkenoyloxy, alkynoyloxy, or aryloyloxy; or I and J taken together form an oxo; and K is hydrogen, hydroxy or lower alkoxy, alkanoyloxy, alkenoyloxy, alkynoyloxy, or aryloyloxy; and P and Q are independently hydrogen or lower alkanoyloxy, alkenoyloxy, alkynoyloxy, or aryloyloxy or P and Q together form an oxo; and S and T are independently hydrogen or lower alkanoyloxy, alkenoyloxy, alkynoyloxy, or aryloyloxy or S and T together form an oxo; and U and V are independently hydrogen or lower alkyl, alkenyl, alkynyl, aryl, or substituted aryl; and W is aryl, substituted aryl, lower alkyl, alkenyl, or alkynyl.

The taxol alkyl groups, either alone or with the various substituents defined hereinabove are preferably lower alkyl containing from one to six carbon atoms in the principal chain and up to 10 carbon atoms. They may be straight or branched chain and include methyl, ethyl, propyl, isopropyl, butyl, isobutyl, tert-butyl, aryl, hexyl, and the like.

The taxol alkenyl groups, either alone or with the various substituents defined hereinabove are preferably lower alkenyl containing from two to six carbon atoms in the principal chain and up to 10 carbon atoms. They may be straight or branched chain and include ethenyl, propenyl, isopropenyl, butenyl, isobutenyl, aryl, hexenyl, and the like.

The taxol alkynyl groups, either alone or with the various substituents defined hereinabove are preferably lower alkynyl containing from two to six carbon atoms in the principal chain and up to 10 carbon atoms. They may be straight or branched chain and include ethynyl, propynyl, butynyl, isobutynyl, aryl, hexynyl, and the like.

Exemplary alkanoyloxy include acetate, propionate, butyrate, valarate, isobutyrate and the like. The more preferred alkanoyloxy is acetate.

The taxol aryl moieties, either alone or with various substituents contain from 6 to 10 carbon atoms and include phenyl, α-naphthyl or β-naphthyl, etc. Substituents include alkanoxy, hydroxy, halogen, alkyl, aryl, alkenyl, acyl, acyloxy, nitro, amino, amido, etc. Phenyl is the more preferred aryl.

"As used herein, the term "aryloyloxy" includes aromatic heterocyclic moieties."

Preferred values of the substituents A, B, D, L, E, F, G, M, I, J, K, P, Q, S, T, U, V, and W are enumerated below in Table I.

TABLE I

| A and B together, form an oxo | A = H | A = OCOR | A = B = H; | | |
|---|---|---|---|---|---|
| L = H | B = OAc, | B = H, | | | |
| D = OH, | L = OH | L = D = H; | | | |
| E = H, | D = H, | | | | |
| F = OAc, | E-OAc, | E and F together form an oxo, | E = H | | |
| | F = H | | F = O (oxetane); | | |
| G and M = CH₂, | G = CH₂, | G = O | G and M together form an oxo, | G = OAc | G = H |
| | M = O (epoxide) | M = CH₂ (epoxide), | | M = CH₂O (oxetane); | M = CH₂O (oxetane); |
| I = J = O, | I = J = H | I-CoPh J = H; | I = COAr J = H; | | |
| K = H, | K = OH, | K = OR, | K-OCOR, | K = OCOAr, | |
| P and Q together, form an oxo | P = H Q = OAc, | P = OCOR Q = H, | P = Q = H; | | |
| S and T together, form an oxo | S = H T-OCOR, | S = H T = OR, | S = OCOR T = H, | S = OR T = H, | S = OH T = H, | S = H T = OH; |
| U = H | U = H | U = H | U = Ph | U = Ar | U = R | U = V = H; |
| V = R, | V = Ph, | V = Ar, | V = H, | V = H, | V = H, | |
| W = R, | W = Ph, | W = Ar; | | | | |

Exemplary compounds within the generic formula are depicted hereinbelow:

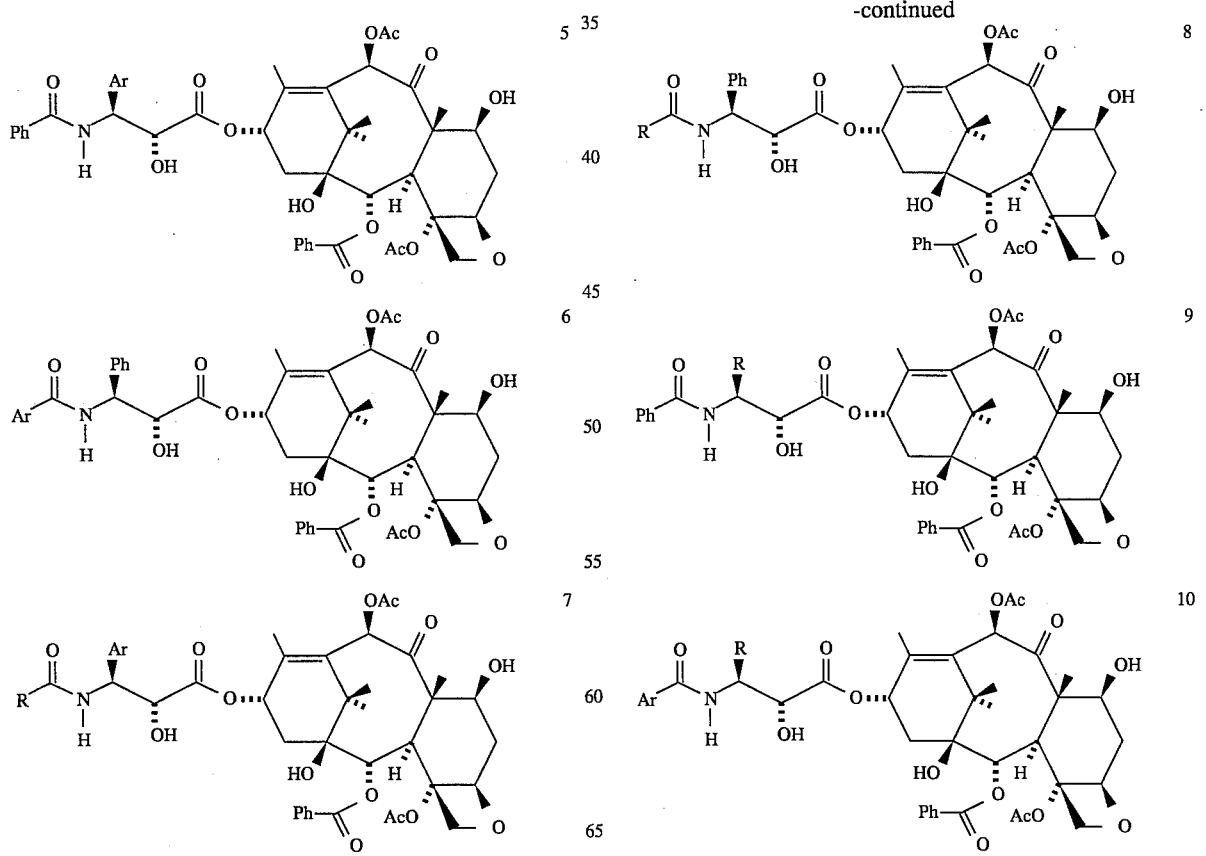

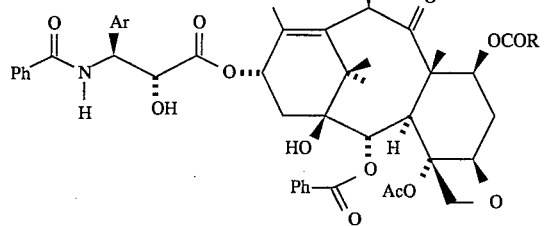
11
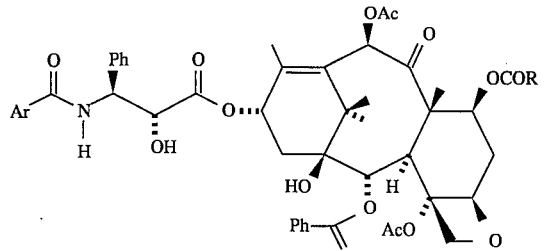
12
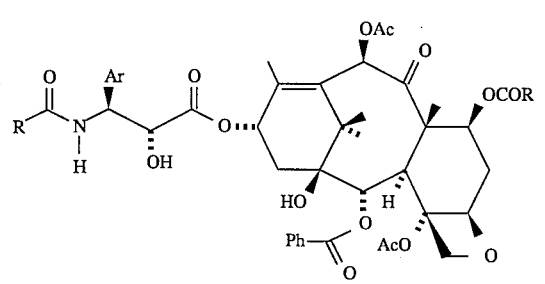
13
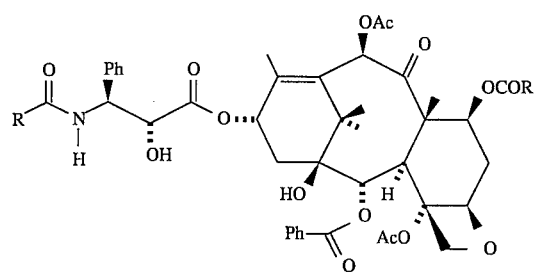
14
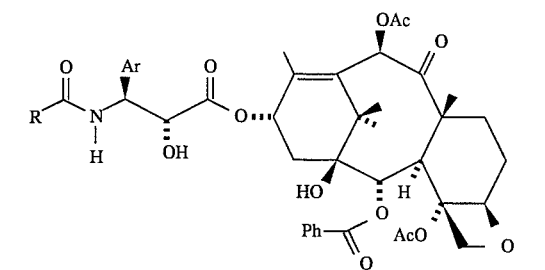
15
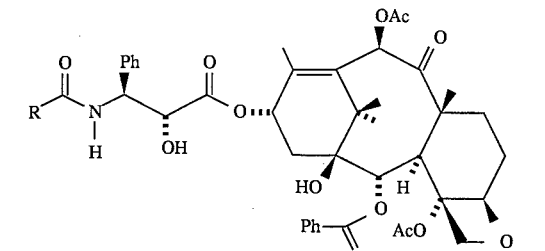
16
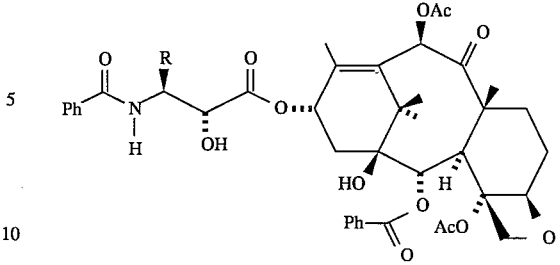
17
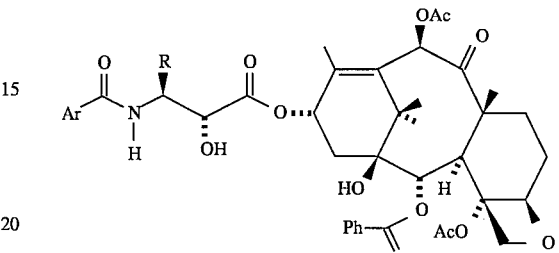
18
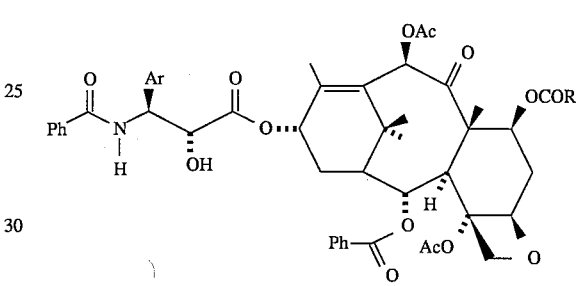
19
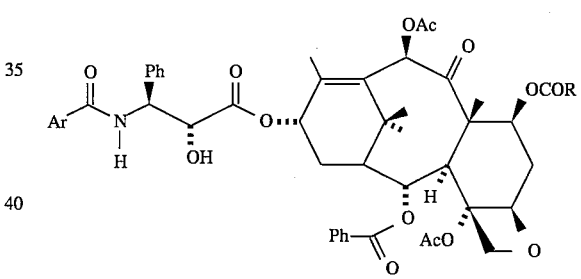
20
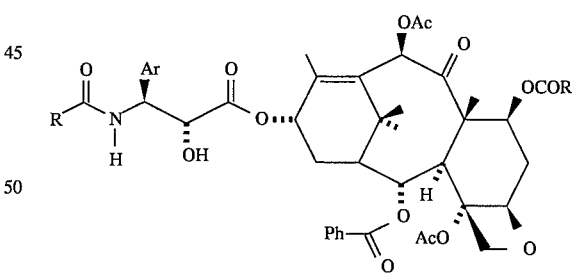
21
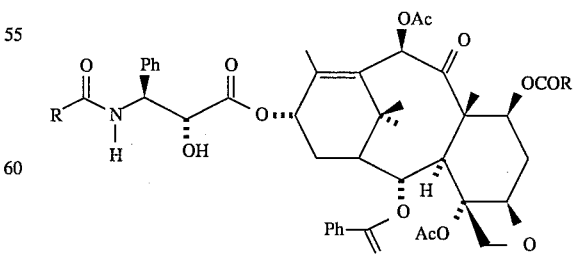
22

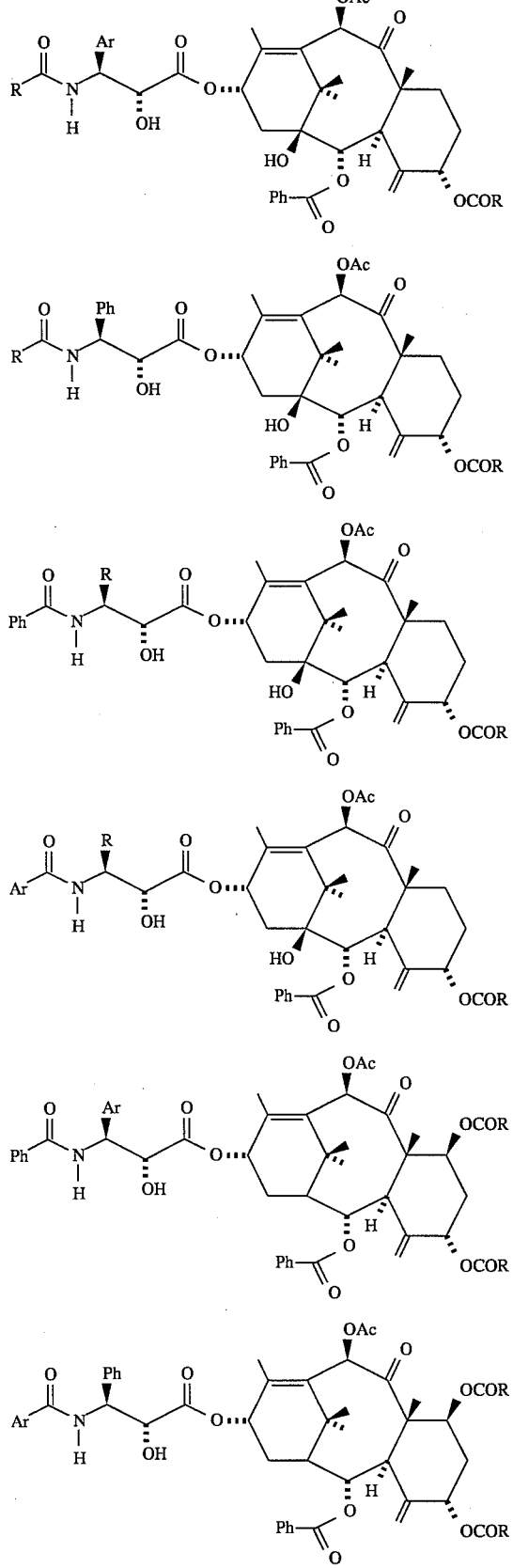

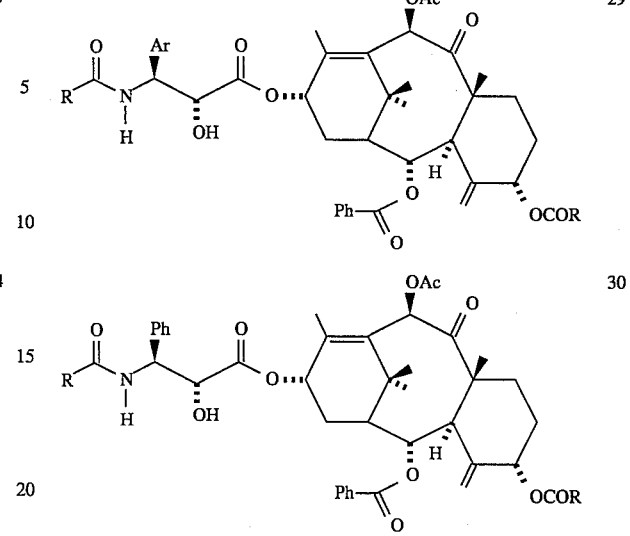

In accordance with the process of the present invention, β-lactams 1 are converted to β-amido esters in the presence of an alcohol and an activating agent, preferably a tertiary amine such as triethyl amine, diisopropyl ethyl amine, pyridine, N-methyl imidizole, and -dimethylaminopyridine (DMAP). For example, β-lactams 1 react with compounds having the taxane tetracyclic nucleus and a C13 hydroxyl group, in the presence of 4-dimethylaminopyridine (DMAP), to provide substances having a β-amido ester group at C13.

Most preferably, the alcohol is 7-O-triethylsilyl baccatin III which can be obtained as described by Greene, et al. in JACS 110, 5917 (1988) or by other routes. As reported in Greene et alo, 10-deacetyl baccatin III is converted to 7-O-triethylsilyl baccatin III according to the following reaction scheme:

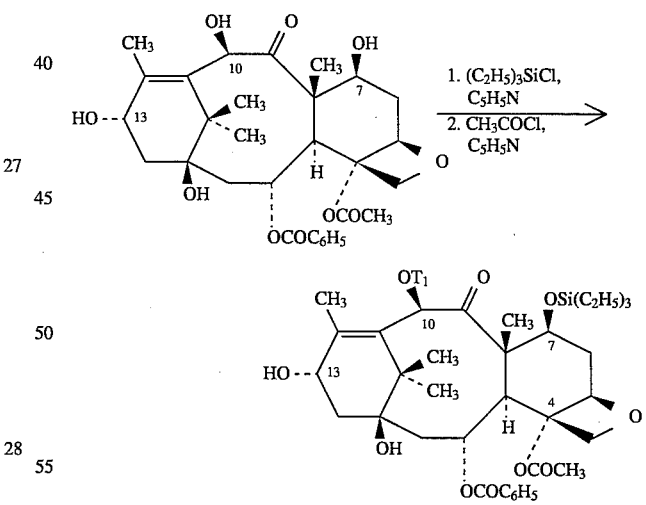

Under what is reported to be carefully optimized conditions, 10-deacetyl baccatin III is reacted with 20 equivalents of $(C_2H_5)_3SiCl_3$ at 23° C. under an argon atmosphere for 20 hours in the presence of 50 mL of pyridine/mmol of 10-deacetyl baccatin III to provide 7-triethylsilyl-10-deacetyl baccatin III (32a) as a reaction product in 84–86% yield after purification. The reaction product is then acetylated with 5 equivalents of $CH_3COCl$ and 25 mL of pyridine/ mmol of 32a at 0° C. under an argon atmosphere for 48 hours to provide 86% yield of 7-O-triethylsilyl baccatin III (32b). Greene, et al. in JACS 110, 5917 at 5918 (1988).

As shown in the following reaction scheme, 7-O-triethylsilyl baccatin III 32b may be reacted with a β-lactam of the present invention at room temperature to provide a taxol intermediate in which the C-7 and C-2' hydroxyl groups are protected with triethylsilyl and ethoxyethyl protecting groups, respectively. These groups are then hydrolyzed under mild conditions so as not to disturb the ester linkage or the taxol substituents.

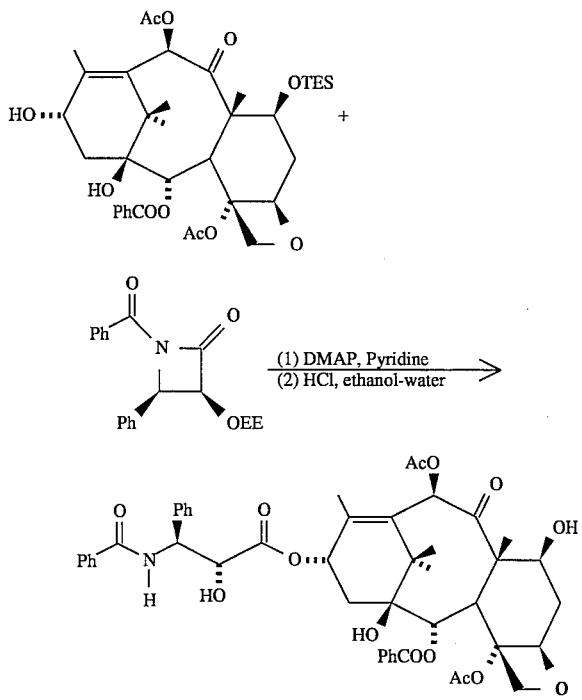

Although the present scheme is directed to the synthesis of the natural product taxol, it can be used with modifications in either the β-lactam or the tetracyclic alcohol, which can be derived from natural or unnatural sources, to prepare other synthetic taxols contemplated within the present invention.

Alternatively, a β-lactam I may be converted to a β-amido ester in the presence of an activating agent and an alcohol other than 7-O-triethylsilyl baccatin III to form a taxol intermediate. Synthesis of taxol may then proceed using the taxol intermediate under an appropriate reaction scheme.

The β-lactam alkyl groups, either alone or with the various substituents defined hereinabove are preferably lower alkyl containing from one to six carbon atoms in the principal chain and up to 15 carbon atoms. They may be straight or branched chain and include methyl, ethyl, propyl, isopropyl, butyl, isobutyl, tert-butyl, aryl, hexyl, and the like.

The β-lactam alkenyl groups, either alone or with the various substituents defined hereinabove are preferably lower alkenyl containing from two to six carbon atoms in the principal chain and up to 15 carbon atoms. They may be straight or branched chain and include ethenyl, propenyl, isopropenyl, butenyl, isobutenyl, aryl, hexenyl, and the like.

The β-lactam alkynyl groups, either alone or with the various substituents defined hereinabove are preferably lower alkynyl containing from two to six carbon atoms in the principal chain and up to 15 carbon atoms. They may be straight or branched chain and include ethynyl, propynyl, butynyl, isobutynyl, aryl, hexynyl, and the like.

Exemplary β-lactam alkanoyloxy include acetate, propionate, butyrate, valarate, isobutyrate and the like. The more preferred alkanoyloxy is acetate.

The β-lactam aryl moieties described, either alone or with various substituents contain from 6 to 15 carbon atoms and include phenyl, α-naphthyl or β-naphthyl, etc. Substituents include alkanoxy, hydroxy, halogen, alkyl, aryl, alkenyl, acyl, acyloxy, nitro, amino, amido, etc. Phenyl is the more referred aryl.

As noted above, $R_2$ of β-lactam 1 may be alkyl, acyl, ethoxyethyl, 2,2,2-trichloroethoxymethyl, or other hydroxyl protecting group such as acetals and ethers, i.e., methoxymethyl, benzyloxymethyl; esters, such as acetates; carbonates, such as methyl carbonates; and the like. A variety of protecting groups for the hydroxyl group and the synthesis thereof may be found in "Protective Groups in Organic Synthesis" by T. W. Greene, John Wiley and Sons, 1981. The hydroxyl protecting group selected should be easily removed under conditions that are sufficiently mild so as not to disturb the ester linkage or other substituents of the taxol intermediate. However, $R_2$ is preferably ethoxyethyl or 2,2,2-trichloroethoxymethyl, and most preferably ethoxyethyl.

Preferred values of the β-lactam substituents $R_1$, $R_2$, and $R_3$ are enumerated herein below:

| | | | | | | |
|---|---|---|---|---|---|---|
| $R_1$ = Ph | $R_1$ = Ar | $R_1$ = p-MeOPh | $R_1$ = alkyl | $R_1$ = alkenyl | $R_1$ = alkynyl | $R_1$ = H |
| $R_2$ = EE | $R_2$ = SiR$_3$ | $R_2$ = alkyl | $R_2$ = OCOR | $R_2$ = MOM | $R_2$ = Cl$_3$CCH$_2$OCH$_2$ | $R_2$ = H |
| $R_3$ = Ph | $R_3$ = Ar | $R_3$ = p-MeOPh | $R_3$ = alkyl | $R_3$ = alkenyl | $R_3$ = alkynyl | $R_3$ = H |

Exemplary compounds within the generic formula are depicted hereinbelow:

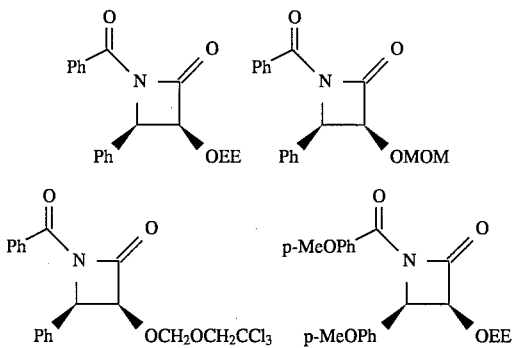

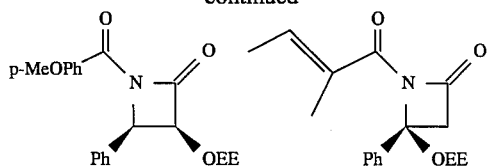

Since the β-lactam 1 has several asymmetric carbons, it is known to those skilled in the art that the compounds of the present invention having asymmetric carbon atoms may exist in diastereomeric, racemic, or optically active forms. All of these forms are contemplated within the scope of this invention. More specifically, the present invention includes enantiomers, diastereomers, racemic mixtures, and other mixtures thereof.

The β-lactams 1 can be prepared from readily available materials, as is illustrated for β-lactam 2 in the scheme below:

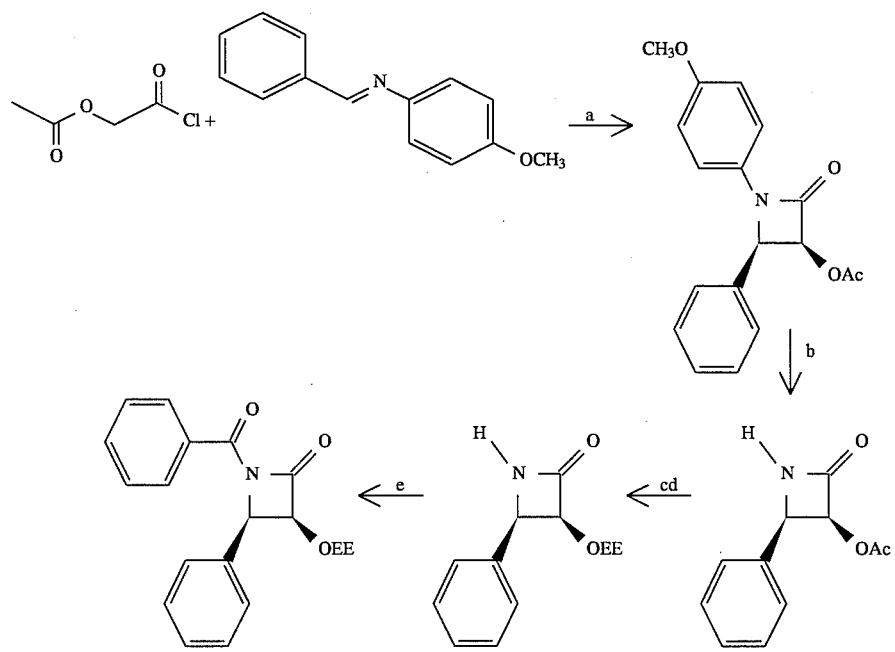

reagents: (a) triethylamine, CH$_2$Cl$_2$, 25° C., 18h; (b) 4 equiv ceric ammonium nitrate, CH$_3$CN, −10° C., 10 min; (c) KOH, THF, H$_2$O, 0° C., 30 min; (d) ethyl vinyl ether, THF, toluene sulfonic acid (cat.), 0° C., 1.5h; (e) CH$_3$Li, ether, −78° C., 10 min; benzoyl chloride, −78° C., 1h.

The starting materials are readily available. α-Acyloxy acetyl chloride is prepared from glycolic acid, and, in the presence of a tertiary amine, it cyclocondenses with imines prepared from aldehydes and p-methoxyaniline to give 1-p-methoxyphenyl-3-acyloxy-4-arylazetidin-2-ones.

The p-methoxyphenyl group can be readily removed through oxidation with ceric ammonium nitrate, and the acyloxy group can be hydrolyzed under standard conditions familiar to those experienced in the art to provide -hydroxy-4-arylazetidin-2-ones.

The 3-hydroxyl group may be protected with a variety of standard protecting groups such as the 1-ethoxyethyl group. Preferably, the racemic 3-hydroxy-4-arylazetidin-2-one is resolved into the pure enantiomers prior to protection by recrystallization of the corresponding 2-methoxy-2-(trifluoromethyl) phenylacetic esters and only the dextrorotatory enantiomer is used in the preparation of taxol. In any event, the 3-(1-ethoxyethoxy)-4-phenylazetidin-2-one can be converted to β-lactam 2, by treatment with a base, preferably n-butyllithium, and an aroyl chloride at −78° C. or below.

The following examples illustrate the invention.

EXAMPLE 1

PREPARATION OF CIS-1-BENZOYL-3-(1-ETHOXYETHOXY)-4-PHENYLAZETIDINONE 2 cis-1-p-methoxyphenyl-3-acetoxy-4-phenylazetidin-2-one. To a solution of 962 mg (4.56 mmol) of the imine derived from benzaldehyde and p-methoxy aniline, and 0.85 mL (6.07 mmol) of triethylamine in 15 mL of CH$_2$Cl$_2$ at −20° C. was added dropwise a solution of 413 mg (3.04 mmol) of α-acetoxy acetyl chloride in 15 mL of CH$_2$Cl$_2$. The reaction mixture was allowed to warm to 25° C. over an 18 h period. The reaction mixture was then diluted with 100 mL of CH$_2$Cl$_2$ and the solution was extracted with 30 mL of 10% aqueous HCl. The organic layer was washed with 30 mL of water and 30 mL of saturated aqueous sodium bicarbonate, dried over sodium sulfate, and concentrated to provide a solid mass. The solid was titurated with 50 mL of hexane and the mixture was filtered. The remaining solid was recrystallized from ethyl acetate/hexane to give 645 mg (68%) of cis-1-p-methoxyphenyl-3-acetoxy-4-phenylazetidin-2-one as white crystals, m.p. 163° C.

cis-3-acetoxy-4-phenylazetidin-2-one. To a solution of 20.2 g of cis-1-p-methoxyphenyl-3-acetoxy-4-phenylazetidin-2-one in 700 mL of acetonitrile at −10° C. was slowly added a solution of ceric ammonium nitrate in 450 mL of water over a 1 h period. The mixture was stirred for 30 min at −10° C. and diluted with 500 mL of ether. The aqueous layer was extracted with two 100 mL portions of ether, and the combined organic layer was washed with two 100 mL portions of water, two 100 mL portions of saturated aqueous sodium bisulfite, two 100 mL portions of saturated aqueous sodium bicarbonate and concentrated to give 18.5 g of a solid. Recrystallization of the solid from acetone/hexane gave 12.3 g (92%) of cis-3-acetoxy-4-phenylazetidin-2-one as white crystals, m.p. 152°–154° C.

cis-3-hydroxy-4-phenylazetidin-2-one. To a mixture of 200 mL of THF and 280 mL of 1 M aqueous potassium hydroxide solution at 0° C. was added a solution of 4.59 g (22.4 mmol) of cis-3-acetoxy-4-phenylazetidin-2-one in 265 ml of THF via a dropping funnel over a 40 min period. The solution was stirred at 0° C. for 1 h and 100 mL of water and 100 mL of saturated sodium bicarbonate were added. The mixture was extracted with four 200 mL portions of ethyl acetate and the combined organic layers were dried over sodium sulfate and concentrated to give 3.54 g (97%) of racemic cis-3-hydroxy-4-phenylazetidin-2-one as white crystals, m.p. 147°–149° C. This material was resolved into its enantiomers by recrystallization of its 2-methoxy-2-(trifluoromethyl)phenylacetic ester from hexane/acetone followed by hydrolysis $[\alpha]^{25}_{Hg}$ 177° C.

cis-3-(1-ethoxyethoxy)-4-phenylazetidin-2-one. To a solution of 3.41 g (20.9 mmol) of cis-3-hydroxy-4-phenylazetidin-2-one in 15 mL of THF at 0° C. was added 5 mL of ethyl vinyl ether and 20 mg (0.2 mmol) of methanesulfonic acid. The mixture was stirred at 0° C. for 20 min, diluted with 20 mL of saturated aqueous sodium bicarbonate, and extracted with three 40 mL portions of ethyl acetate. The combined ethyl acetate layers were dried over sodium sulfate and concentrated to give 4.87 g (99%) of cis-3-(1-ethoxyethoxy)-4-phenylazetidin-2-one as a colorless oil.

cis-1-benzoyl-3-(1-ethoxyethoxy)-4-phenylazetidin-2-one. To a solution of 2.35 g (10 mmol) of cis-3-(1-ethoxyethoxy)-4-phenylazetidin-2-one in 40 mL of THF at −78° C. was added 6.1 mL (10.07 mmol) of a 1.65 M solution of n-butyllithium in hexane. The mixture was stirred for 10 min at −78° C. and a solution of 1.42 g (10.1 mmol) of benzoyl chloride in 10 mL of THF was added. The mixture was stirred at −78° C. for 1 h and diluted with 70 mL of saturated aqueous sodium bicarbonate and extracted with three 50 mL portions of ethyl acetate. The combined ethyl acetate extracts were dried over sodium sulfate and concentrated to give 3.45 g of an oil. Chromatography of the oil on silica gel eluted with ethyl acetate/hexane gave 3.22 g (95%) of cis-1-benzoyl-3-(1-ethoxyethoxy)-4-phenylazetidin-2-one (2) as a colorless oil.

EXAMPLE 2

PREPARATION OF β-AMIDO ESTERS FROM CIS-1-BENZOYL-3-(1-ETHOXYETHOXY)-4-PHENYLAZETIDIN-2-ONE 2

Benzyl-3-benzamido-3-phenyl-2-hydroxyproionate. To a solution of 88 mg (0.26 mmol) of cis-1-benzoyl-3-(1-ethoxyethoxy)-4-phenylazetidin-2-one in 0.3 mL of THF was added 28 mg (0.26 mmol) of benzyl alcohol and 32 mg (0.26 mmol) of 4-dimethylamino pyridine (DMAP). After 5 h at 25° C. the mixture was diluted with 10 mL of saturated aqueous sodium bicarbonate solution and extracted with three 20 mL portions of ethyl acetate. The combined ethyl acetate layers were extracted with 10 mL of 5% aqueous HCl and 10 mL of saturated sodium bicarbonate, dried over sodium sulfate and concentrated to give 112 mg (100%) of benzyl ester as an oil which was >97% pure by NMR analysis. To a solution of this oil in 4 mL of THF was added 1 mL of 10% aqueous HCl solution. The mixture was stirred at 25° C. for 30 min, diluted with 20 mL of saturated aqueous sodium bicarbonate solution, and extracted with four 30 mL portions of ethyl acetate. The combined ethyl acetate extracts were dried over sodium sulfate and concentrated to provide a solid. Recrystallization of the solid from chloroform gave 92 mg (95%) of benzyl-3-benzamido-3-phenyl-2-hydroxypropionate as white crystals, m.p. 129°–131° C.

Taxol. To a small reaction vessel was added 109 mg (0.320 mmol) of (+)-cis-1-benzoyl-3-(1-ethoxyethoxy-4-phenyl-aretidin-2-one, 45 mg (0.064 mmol) of 7-O-triethylsilyl baccatin III, 7.8 mg (0.064 mmol) of 4-dimethylamino pyridine (DMAP) and 0.032 mL of pyridine. The mixture was stirred at 25° C. for 12 h and diluted with 100 mL of ethyl acetate. The ethyl acetate solution was extracted with 20 mL of 10% aqueous copper sulfate solution, dried over sodium sulfate and concentrated. The residue was filtered through a plug of silica gel eluted with ethyl acetate. Flash chromatography on silica gel eluted with ethyl acetate/hexane follwed by recrystallization from ethyl acetate/hexane gave 61 mg (92%) of 2'-(1-ethoxyethoxy)-7-O-triethylsilyl taxol as a 2:1 mixture of diastereomers.

A 5 mg sample of 2'-(1-ethoxyethoxy)-7-O-triethylsilyl taxol was dissolved in 2 mL of ethanol and 0.5 mL of 0.5% aqueous HCl solution was added. The mixture was stirred at 0° C. for 30 h and diluted with 50 mL ethyl acetate. The solution was extracted with 20 mL of saturated aqueous sodium bicarbonate solution, dried over sodium sulfate and concentrated. The residue was purified by column chromatography on silica gel eluted with ethyl acetate/hexane to provide 13 mg (ca. 90%) of taxol, which was identical with an authentic sample in all respects.

In view of the above, it will be seen that the several objects of the invention are achieved.

As various changes could be made in the above compositions and processes without departing from the scope of the invention, it is intended that all matter contained in the above description be interpreted as illustrative and not in a limiting sense.

What is claimed is:

1. A cis diastereomer of a β-lactam having the formula:

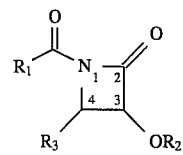

wherein $R_1$ is phenyl, naphthyl, substituted phenyl, alkyl, alkenyl, or alkynyl; $R_2$ is ethoxyethyl, 2,2,2-trichloroethoxymethyl or other hydroxyl protecting group; and $R_3$ is phenyl, naphthyl, substituted phenyl, alkyl, alkenyl, or alkynyl.

2. The diastereomer of claim 1 wherein the hydroxyl protecting group is selected from the group consisting of ethers, esters, and carbonates.

3. A cis diastereomer of a β-lactam having the formula:

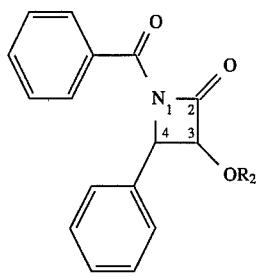

wherein $R_2$ is a hydroxyl protecting group.

4. A cis diastereomer of a β-lactam having the formula:

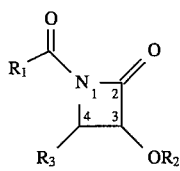

wherein $R_1$ is phenyl, substituted phenyl or alkyl, $R_2$ is a hydroxyl protecting group, and $R_3$ is phenyl, substituted phenyl, alkyl, alkenyl, or alkynyl.

5. The diastereomer of claim 1 wherein the substituents of said substituted phenyl are selected from alkanoxy, halogen, alkyl, aryl, alkenyl, nitro, and amino.

6. The diastereomer of claim 1 wherein $R_1$ is phenyl or substituted phenyl.

7. The diastereomer of claim 4 wherein the hydroxyl protecting group is selected from the group consisting of ethers, esters, and carbonates.

8. The diastereomer of claim 3 wherein $R_2$ is selected from the group consisting of ethers, esters, and carbonates.

9. The diastereomer of claim 1 wherein $R_3$ is phenyl, substituted phenyl, alkyl or alkenyl.

10. The diastereomer of claim 1 wherein $R_3$ is alkyl, alkenyl, phenyl or substituted phenyl wherein the substituents of said substituted phenyl are selected from alkanoxy, halogen, alkyl, aryl, alkenyl, nitro, and amino.

11. The diastereomer of claim 4 wherein $R_1$ is phenyl or substituted phenyl.

12. The diastereomer of claim 4 wherein $R_3$ is alkyl, alkenyl, phenyl or substituted phenyl wherein the substituents of said substituted phenyl are selected from alkanoxy, halogen, alkyl, aryl, alkenyl, nitro, and amino.

13. A β-lactam having the formula:

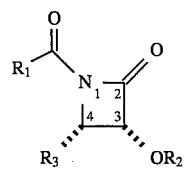

wherein $R_1$ is phenyl, naphthyl, substituted phenyl, alkyl, alkenyl, or alkynyl; $R_2$ is a hydroxyl protecting group; and $R_3$ is phenyl, naphthyl, substituted phenyl, alkyl, alkenyl, or alkynyl.

14. A β-lactam of claim 13 wherein the hydroxyl protecting group is selected from the group consisting of ethers, esters, and carbonates.

15. A β-lactam of claim 13 wherein the substituents of said substituted phenyl are selected from alkanoxy, halogen, alkyl, aryl, alkenyl, nitro and amino.

16. A β-lactam of claim 15 wherein $R_1$ is phenyl or substituted phenyl.

17. A β-lactam of claim 16 wherein $R_3$ is phenyl, substituted phenyl, alkyl or alkenyl.

18. A β-lactam of claim 15 wherein $R_3$ is phenyl, substituted phenyl, alkyl or alkenyl.

19. The diastereomer of claim 13 wheremn $R_1$ and are, independently, phenyl or substituted phenyl.

* * * * *

UNITED STATES PATENT AND TRADEMARK OFFICE
CERTIFICATE OF CORRECTION

| | | |
|---|---|---|
| PATENT NO. | : 5,574,156 | Page 1 of 3 |
| APPLICATION NO. | : 08/254561 | |
| DATED | : November 12, 1996 | |
| INVENTOR(S) | : Robert A. Holton | |

It is certified that error appears in the above-identified patent and that said Letters Patent is hereby corrected as shown below:

On the Face of the Patent
   The Title should read -- CIS-DIASTEREOMERS OF N-ACYLATED β-LACTAMS --.
   (63) Related U.S. Application Data, should read: -- Division of Ser. No. 07/968,003, Oct. 26, 1992, Pat. No. 5,336,785, which is a continuation of Ser. No. 07/415,028, Sep. 29, 1989, Pat. 5,175,315, which is a continuation-in-part of Ser. No. 07/359,634, May 31, 1989, abandoned. This application is also a continuation of Ser. No. 07/967,998, Oct. 26, 1992, abandoned, which is a division of Ser. No. 07/415,028, Sep. 29, 1989, Pat. No. 5,175,315, which is a continuation-in-part of Ser. No. 07/359,634, May 31, 1989, abandoned. U.S. Serial No. 07/967,998, is also a division of Ser. No. 07/949,107, Sep. 22, 1992, abandoned. --.

Column 1
   Lines 11-23 should read: -- This application is a divisional of U.S. Ser. No. 07/968,003, filed Oct. 26, 1992, now U.S. Pat. No. 5,336,785, which is a continuation of U.S. Ser. No. 07/415,028, filed Sep. 29, 1989, now U.S. Pat. 5,175,315, which is a continuation-in-part of U.S. Ser. No. 07/359,634, filed May 31, 1989, now abandoned. This application is also a continuation of U.S. Ser. No. 07/967,998, filed Oct. 26, 1992, now abandoned, which is a divisional of U.S. Ser. No. 07/415,028, filed Sep. 29, 1989, now Pat. No. 5,175,315, which is a continuation-in-part of U.S. Ser. No. 07/359,634, filed May 31, 1989, now abandoned. U.S. Serial No. 07/967,998, is also a divisional of U.S. Ser. No. 07/949,107, filed Sep. 22, 1992, now abandoned. --.

Lines 35-45, the chemical structure should read

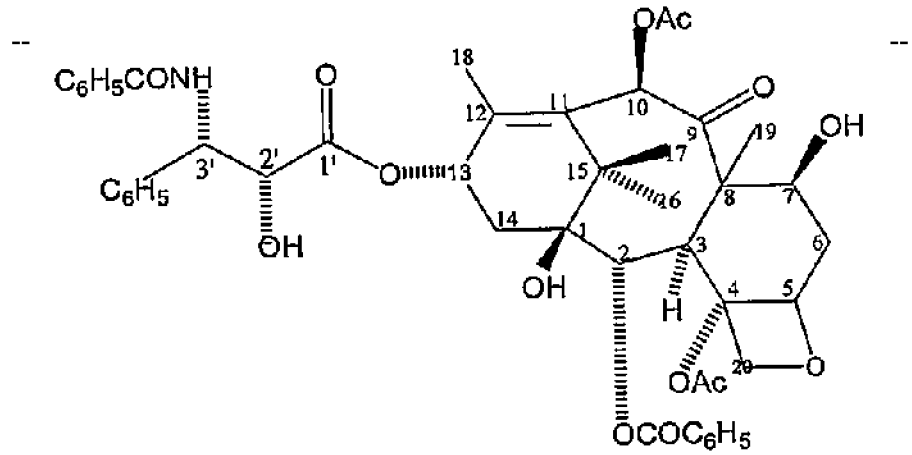

Column 2
   Line 50, "of the" should read -- of the formula: --.
   Line 51, the chemical structure should be labeled -- 1 --.

UNITED STATES PATENT AND TRADEMARK OFFICE
CERTIFICATE OF CORRECTION

PATENT NO.         : 5,574,156
APPLICATION NO. : 08/254561
DATED                   : November 12, 1996
INVENTOR(S)        : Robert A. Holton It is certified that error appears in the above-identified patent and that said Letters Patent is hereby corrected as shown below:

Column 3
      Line 20, the chemical structure should be labeled -- 1 --.

Column 4
      Lines 1-9, the chemical structure should read

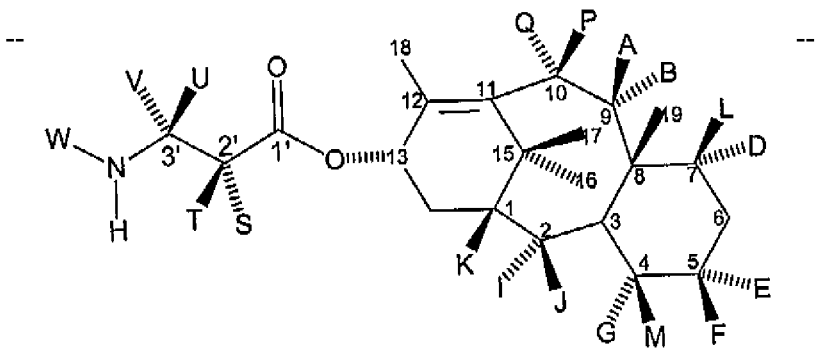

Column 5
      Table I, the 11th line of the table, the portion reading "I-CoPh" should read -- I-COPh --.

Column 10
      Lines 39-47, below the chemical structure, it should be labeled -- 31 --.
      Lines 48-55, below the chemical structure, it should be labeled
-- 32  a. R = H
     b. R = $COCH_3$ --.

Column 11
      Lines 13-20, below the first recited chemical structure, it should be labeled
-- 32b --
      Lines 22-27, below the second recited chemical structure, it should be labeled
-- 2 --.
      Lines 29-39, below the third recited chemical structure, it should be labeled
-- TAXOL --.

Column 12
      Line 20, "referred" should read -- preferred --.

UNITED STATES PATENT AND TRADEMARK OFFICE
CERTIFICATE OF CORRECTION

PATENT NO.        : 5,574,156
APPLICATION NO. : 08/254561
DATED              : November 12, 1996
INVENTOR(S)       : Robert A. Holton It is certified that error appears in the above-identified patent and that said Letters Patent is hereby corrected as shown below:

Column 13
 Lines 1-8 the chemical structure should read

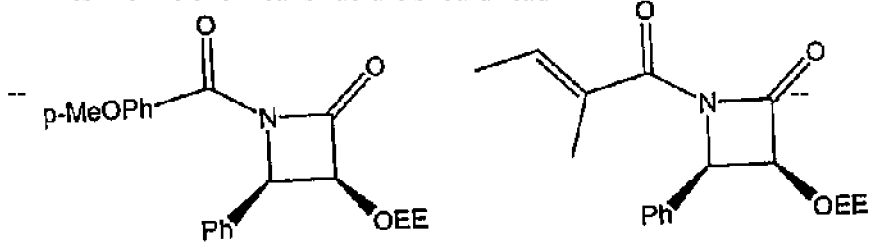

Column 15
 Line 8, "ml" should read -- mL --.

Column 18
 Claim 19, line 36, "wheremn $R_1$ and are," should read -- wherein $R_1$ and $R_3$ are, --.

Signed and Sealed this

Twelfth Day of June, 2007

JON W. DUDAS
*Director of the United States Patent and Trademark Office*